US009421264B2

(12) United States Patent
Wardell et al.

(10) Patent No.: US 9,421,264 B2
(45) Date of Patent: Aug. 23, 2016

(54) METHOD OF TREATING CANCER USING SELECTIVE ESTROGEN RECEPTOR MODULATORS

(71) Applicant: Duke University, Durham, NC (US)

(72) Inventors: Suzanne E. Wardell, Durham, NC (US); Erik R. Nelson, Champaign, IL (US); Donald P. McDonnell, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/512,061

(22) Filed: Oct. 10, 2014

(65) Prior Publication Data

US 2015/0274640 A1    Oct. 1, 2015

Related U.S. Application Data

(60) Provisional application No. 61/971,627, filed on Mar. 28, 2014.

(51) Int. Cl.

| *A61K 31/136* | (2006.01) |
|---|---|
| *A61K 31/137* | (2006.01) |
| *A61K 31/138* | (2006.01) |
| *C07C 217/78* | (2006.01) |
| *C07C 217/84* | (2006.01) |
| *A61K 45/06* | (2006.01) |
| *A61K 31/40* | (2006.01) |
| *A61K 31/4196* | (2006.01) |
| *A61K 31/4535* | (2006.01) |
| *A61K 31/565* | (2006.01) |
| *A61K 31/5685* | (2006.01) |

(52) U.S. Cl.
CPC .............. *A61K 45/06* (2013.01); *A61K 31/136* (2013.01); *A61K 31/137* (2013.01); *A61K 31/138* (2013.01); *A61K 31/40* (2013.01); *A61K 31/4196* (2013.01); *A61K 31/4535* (2013.01); *A61K 31/565* (2013.01); *A61K 31/5685* (2013.01); *C07C 217/78* (2013.01); *C07C 217/84* (2013.01)

(58) Field of Classification Search
CPC . A61K 31/136; A61K 31/137; A61K 31/138; A61K 31/40; A61K 31/4196; A61K 31/4535; A61K 31/565; A61K 31/5685; A61K 45/06; C07C 217/78; C07C 217/84
See application file for complete search history.

(56) References Cited

U.S. PATENT DOCUMENTS

| 7,612,114 B2 | 11/2009 | Hamaoka et al. |
| 7,960,412 B2 | 6/2011 | Hamaoka et al. |
| 8,399,520 B2 | 3/2013 | Hamaoka et al. |
| 2006/0116364 A1 | 6/2006 | Hamaoka et al. |

OTHER PUBLICATIONS

Pors et al. 1991, Journal of Neuro-Oncology, vol. 10, pp. 173-177.*
Perey et al. 2007, Annals of Oncology, vol. 18, pp. 64-69.*
Wu and Wu, J. Biol. Chem. (1987) 262:4429-4432.
Chang et al., Methods Enzymol. (2003) 364:118-42.
Huang et al., Mol. Endocrinol. (2002) 16(8):1778-92.
Connor et al., Cancer Res. (2001) 61(7):2917-22.
Chang et al., Mol Cell Biol. (1999) 19(12):8226-39.
Norris et al., Science (1999) 285(5428):744-6.
International Search Report and Written Opinion for Application No. PCT/US2015/023216 dated Jun. 24, 2015 (12 pages).
Deshmane et al., "Phase III Double-Blind Trial of Arzoxifene Compared With Tamoxifen for Locally Advanced or Metastatic Breast Cancer," Journal of Clinical Oncology, 2007, vol. 25, No. 31, pp. 4967-4973.
Johnston et al., "Endocrine Manipulation in Advanced Breast Cancer: Recent Advances with SERM Therapies," Clinical Cancer Research, 2001, vol. 7, pp. 4376s-4387s.
Gradishar et al., "Effects of High Dose Raloxifene in Selected Patients with Advanced Breast Carcinoma," Cancer, 2000, vol. 88, No. 9, pp. 2047-2053.
Baumann et al., "Estrogen Receptor Modulators and Down Regulators" Drugs 2007; 67 (16): 2335-2353.
Orlando et al., "Molecularly targeted endocrine therapies for breast cancer" Cancer Treatment Reviews 36S3 (2010) S67-S71.
O'Regan et al., "The evolution of tamoxifen therapy in breast cancer: selective oestrogen-receptor modulators and downregulators" The Lancet Oncology vol. 3 Apr. 2002, 207-214.
Radius Health, "Radius Initiates Phase 2a Clinical Trial of RAD1901 in Menopausal Hot Flashes" <http://www.ornewswire.com/news-releases/radius-initiates-phase-2a-clinical-trial-of-rad1901-in-menopausal-hot-flashes-61919867.html> Mar. 24, 2009.
Radius Health, "Radius Presents Positive Phase 2a Study Results Establishing Clinical Proof of Concept for RAD1901 in Reducing Menopausal Hot Flashes" Press release, 2010, 2 pages.
Hattersley et al., "RAD-1901, a Novel SERM, has Efficacy in an Animal Model of Vasomotor Symptoms" Endocrine Society Meeting, 2007, 1 page.

* cited by examiner

*Primary Examiner* — Kara R McMillian
(74) *Attorney, Agent, or Firm* — Michael Best & Friedrich LLP (57) ABSTRACT

Disclosed herein are methods of treating subjects suffering from estrogen receptor positive cancer of the brain by administering a selective estrogen receptor degrader (SERM). Also disclosed are methods of treating a cancer that is resistant to an estrogen receptor modulator by administering a SERM.

28 Claims, 4 Drawing Sheets

METHOD OF TREATING CANCER USING SELECTIVE ESTROGEN RECEPTOR MODULATORS

CROSS REFERENCE TO RELATED APPLICATIONS

This application claims priority to U.S. Provisional Application No. 61/971,627, filed Mar. 28, 2014, which is incorporated herein by reference in its entirety.

STATEMENT OF GOVERNMENT INTEREST

Not applicable.

TECHNICAL FIELD

The present invention relates to methods of treating subjects suffering from estrogen receptor positive cancer of the brain by administering a selective estrogen receptor modulator (SERM) to the subject. The present invention also relates to methods of treating subjects suffering from a cancer that is resistant to an estrogen receptor modulator by administering a SERM to the subject.

BACKGROUND

The estrogen receptor (ER) is a ligand dependent transcription factor whose expression confers upon target cells the ability to respond to estrogens. In the absence of an activating ligand, ER resides in the cell in an inactive form within a large inhibitory protein complex. Upon binding ligand, however, the receptor undergoes an activating conformational change resulting in its release from the inhibitory protein complex, spontaneous dimerization and subsequent interaction with enhancers located within target genes. Depending on the promoter context of the bound receptor, and the co factors that are recruited to the receptor in a particular cell, it can either positively or negatively regulate target gene transcription. Thus, the same ER-ligand complex can have very different activities in different cells, an observation that explains how estrogens, generally considered to be reproductive hormones, exhibit activities in bone, the cardiovascular system and in brain that are unrelated to reproductive function.

Whereas the molecular determinants of ER action differ considerably between target cells, it has been anticipated that the exploitation of this complexity will yield pharmaceuticals with process or tissue selective activities. The first evidence in support of this hypothesis came from studies that probed the pharmacological activities of the 'antiestrogen' tamoxifen. Identified as a high affinity antagonist of ER and developed as a treatment for ER-positive breast cancer, it soon became apparent that whereas tamoxifen could oppose estrogen action in the breast it exhibited agonist activity in the bone, uterus and in the cardiovascular system. Reflecting this spectrum of activities, tamoxifen was reclassified as a Selective Estrogen Receptor Modulator (SERM).

The increasing incidence of breast cancer brain metastases (BCBM) is an emerging challenge in the treatment of advanced breast cancer patients. The growing success of improved treatments of systemic disease has allowed the manifestation of BCBM that previously would not have impacted the morbidity and mortality associated with breast cancer. The privileged environment of the brain, maintained by the relatively non-porous blood brain barrier, presents a significant impediment to the successful targeting of BCBM, leading to the use of gamma knife surgery and/or whole brain radiation in an attempt to shrink or ablate brain lesions. The benefit of these treatments must be carefully balanced with neurological deficit as a result of treatment.

Although considerable advances have been made in targeting the estrogen signaling axis for the treatment of breast cancer and osteoporosis, similar progress has unfortunately not yet been accomplished in the development of safe and effective treatments for the climacteric conditions or vasomotor disturbances that are associated with estrogen deprivation. There is considerable interest in developing novel SERMs that can be used to treat vasomotor symptoms but which do not exhibit mitogenic activities in the breast or the uterus.

While tamoxifen and aromatase inhibitors have proven effective in the treatment of estrogen receptor positive (ER+) breast cancer, the incidence of resistance remains significant, particularly in the advanced/metastatic breast cancer setting. An additional class of estrogen receptor targeting therapy, selective estrogen receptor degraders (SERDs), has recently come to prominence. These agents have proven effective in pre-clinical models of breast cancers that are resistant to tamoxifen or aromatase inhibitors, leading to their evaluation in clinical trials. However, these agents also do not readily pass the blood brain barrier, suggesting that they will be ineffective in targeting BCBM. It would be beneficial to have other treatment options that can penetrate the blood brain barrier and/or selectively target tissue specific activities responsive to ER activation.

SUMMARY

The present invention is directed to a method of treating estrogen receptor positive cancers of the brain in a subject. The method comprises administering a compound represented by the following formula I:

wherein

TZ represents a C1-C4 alkylene group or —CR$^{f'}$R$^{g'}$—CH2-O— wherein R$^{f'}$ and R$^{g'}$ independently represent hydrogen or a C1-C6 alkyl group;

A represents a 5- to 14-membered heteroarylene group which may have a substituent or a C6-C14 arylene group which may have a substituent;

Y represents —CH$_2$—NR$^c$— wherein R$^c$ represents hydrogen or a C1-C6 alkyl group which may have a substituent;

ring G represents the following formula:

R' represents 1 to 4 substituents independently selected from a hydrogen atom, a C1-C6 alkoxy group, and a hydroxyl group;

a partial structure in formula (I) represented by the following formula:

is

R" represents hydrogen, a hydroxyl group that may be further protected by a protecting group or a C1-C6 alkoxy group which may have a substituent; and $R^a$ and $R^b$ are the same as or different from each other and each represents a hydrogen atom, a C1-C6 alkyl group which may have a substituent, or a C3-C8 cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and L represents a single bond,
or a salt thereof.

The cancer may be Breast cancer brain metastases, Astrocytoma, Atypical Teratoid Rhabdoid Tumor (ATRT), Chondrosarcoma, Choroid Plexus Carcinoma, Craniopharyngioma, Ependymoma, Germ Cell Tumor, Glioblastoma, Glioma, Hemangioma, Juvenile Pilocytic Astrocytoma, Medulloblastoma, Meningioma, Neurofibroma, Neuronal and Mixed Neuronal-Glial Tumors, Oligoastrocytoma, Oligodendroglioma, Pineal Tumor, Pituitary Tumor, PNET— (primitive neuroectodermal tumor), Schwannoma, and Leptomeningeal metastases. $R^a$ and $R^b$ independently may represent a hydrogen atom, a methyl group, an ethyl group, a n-propyl group, an iso-propyl group, a n-butyl group, an iso-butyl group, or a tert-butyl group. -T-Z— may represents —CH$_2$CH$_2$— or —C(CH$_3$)$_2$CH$_2$O—. Y may represents —CH2-N(CH$_2$CH$_3$)— or —CH$_2$—N(CH$_2$CH$_2$OH)—. Each of R" independently may represents a hydrogen atom or a methoxy group. R" may represents a hydroxyl group. A may represents a phenylene group. The compound may be (R)-6-{2-{ethyl[4-(2-ethylaminoethyl)benzyl]amino}-4-methoxyphenyl}-5,6,7,8-tetrahydronaphthalen-2-ol. An effective amount of the compound may be administered. The effective amount may comprise a high dosage. The high dosage may be more than about 20 mg/kg. The high dosage may be about 20 mg/kg to about 100 mg/kg. The compound may be administered by oral administration, intravenous administration, intradermal injection, intramuscular injection or subcutaneous injection. The method may further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

The present invention is directed to a method of treating breast cancer brain metastasis in a subject. The method comprises administering a compound represented by the following formula I:

wherein

TZ represents a C1-C4 alkylene group or —CR$^{f'}$R$^{g'}$—CH2-O— wherein R$^{f'}$ and R$^{g'}$ independently represent hydrogen or a C1-C6 alkyl group;

A represents a 5- to 14-membered heteroarylene group which may have a substituent or a C6-C14 arylene group which may have a substituent;

Y represents —CH$_2$—NR$^c$— wherein R$^c$ represents hydrogen or a C1-C6 alkyl group which may have a substituent;

ring G represents the following formula:

R' represents 1 to 4 substituents independently selected from a hydrogen atom, a C1-C6 alkoxy group, and a hydroxyl group;

a partial structure in formula (I) represented by the following formula:

R" represents hydrogen, a hydroxyl group that may be further protected by a protecting group or a C1-C6 alkoxy group which may have a substituent; and

$R^a$ and $R^b$ are the same as or different from each other and each represents a hydrogen atom, a C1-C6 alkyl group which may have a substituent, or a C3-C8 cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and L represents a single bond,
or a salt thereof.

$R^a$ and $R^b$ independently may represent a hydrogen atom, a methyl group, an ethyl group, a n-propyl group, an iso-propyl group, a n-butyl group, an iso-butyl group, or a tert-butyl group. -T-Z— may represents —CH$_2$CH$_2$— or —C(CH$_3$)$_2$CH$_2$O—. Y may represents —CH2-N(CH$_2$CH$_3$)— or —CH$_2$—N(CH$_2$CH$_2$OH)—. Each of R"

independently may represents a hydrogen atom or a methoxy group. R" may represents a hydroxyl group. A may represents a phenylene group. The compound may be (R)-6-{2-{ethyl[4-(2-ethylaminoethyl)benzyl]amino}-4-methoxyphenyl}-5,6,7,8-tetrahydronaphthalen-2-ol. An effective amount of the compound may be administered. The effective amount may comprise a high dosage. The high dosage may be more than about 20 mg/kg. The high dosage may be about 20 mg/kg to about 100 mg/kg. The compound may be administered by oral administration, intravenous administration, intradermal injection, intramuscular injection or subcutaneous injection. The method may further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

The present invention is directed to a method of treating a cancer in a subject, wherein the cancer is resistant to an estrogen receptor modulator. The method comprises administering a compound represented by the following formula I:

(I)

wherein

TZ represents a C1-C4 alkylene group or —CR$^f$R$^{g'}$—CH2-O— wherein R$^f$ and R$^{g'}$ independently represent hydrogen or a C1-C6 alkyl group;

A represents a 5- to 14-membered heteroarylene group which may have a substituent or a C6-C14 arylene group which may have a substituent;

Y represents —CH$_2$—NR$^c$— wherein R$^c$ represents hydrogen or a C1-C6 alkyl group which may have a substituent;

ring G represents the following formula:

R' represents 1 to 4 substituents independently selected from a hydrogen atom, a C1-C6 alkoxy group, and a hydroxyl group;

a partial structure in formula (I) represented by the following formula:

R" represents hydrogen, a hydroxyl group that may be further protected by a protecting group or a C1-C6 alkoxy group which may have a substituent; and R$^a$ and R$^b$ are the same as or different from each other and each represents a hydrogen atom, a C1-C6 alkyl group which may have a substituent, or a C3-C8 cycloalkyl group which may have a substituent, or when R$^a$ and R$^b$ are bonded together, they may form, together with the nitrogen atom that is adjacent to R$^a$ and R$^b$, a 4- to 10-membered single ring which may have a substituent; and L represents a single bond, or a salt thereof.

The cancer may be de novo resistant to the estrogen receptor modulator. The resistance to the estrogen receptor modulator may be acquired. The estrogen receptor modulator may be a selective estrogen receptor modulator (SERM). The SERM may be tamoxifen, idoxifene, raloxifene or ICI 182,780. The cancer may be breast, endometrial or ovarian cancer. The cancer may be breast cancer. R$^a$ and R$^b$ independently may represent a hydrogen atom, a methyl group, an ethyl group, a n-propyl group, an iso-propyl group, a n-butyl group, an iso-butyl group, or a tert-butyl group. -T-Z— may represents —CH$_2$CH$_2$— or —C(CH$_3$)$_2$CH$_2$O—. Y may represents —CH2-N(CH$_2$CH$_3$)— or —CH$_2$—N(CH$_2$CH$_2$OH)—. Each of R" independently may represents a hydrogen atom or a methoxy group. R" may represents a hydroxyl group. A may represents a phenylene group. The compound may be (R)-6-{2-{ethyl[4-(2-ethylaminoethyl)benzyl]amino}-4-methoxyphenyl}-5,6,7,8-tetrahydronaphthalen-2-ol. An effective amount of the compound may be administered. The effective amount may comprise a high dosage. The high dosage may be more than about 20 mg/kg. The high dosage may be about 20 mg/kg to about 100 mg/kg. The compound may be administered by oral administration, intravenous administration, intradermal injection, intramuscular injection or subcutaneous injection. The method may further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

BRIEF DESCRIPTION OF THE DRAWINGS

FIG. 2A shows ERα protein expression in whole cell extracts pre-treated with transcription or translation inhibitors before treatment with RAD1901, analyzed by immunoblot. FIG. 2B shows ERα mRNA expression in similarly treated cells.

DETAILED DESCRIPTION

The present disclosure provides a method of treating a subject suffering from estrogen receptor positive cancer of the brain, such as BCBM, or a cancer that is resistant to an estrogen receptor modulator, such as tamoxifen resistant breast cancer. The methods involve administering to the subject a SERM, such as RAD 1901. RAD 1901 exhibits desired pharmacological activities and exhibits significant brain penetrance when evaluated in post-menopausal women, in particular a unique dose response, with lower doses of the drug being more effective at relieving hot flashes. RAD 1901 induces hot flashes in healthy postmenopausal women in a dose dependent manner, thus RAD 1901 may effectively inhibit estrogen receptor action in the brain.

Figure 1:
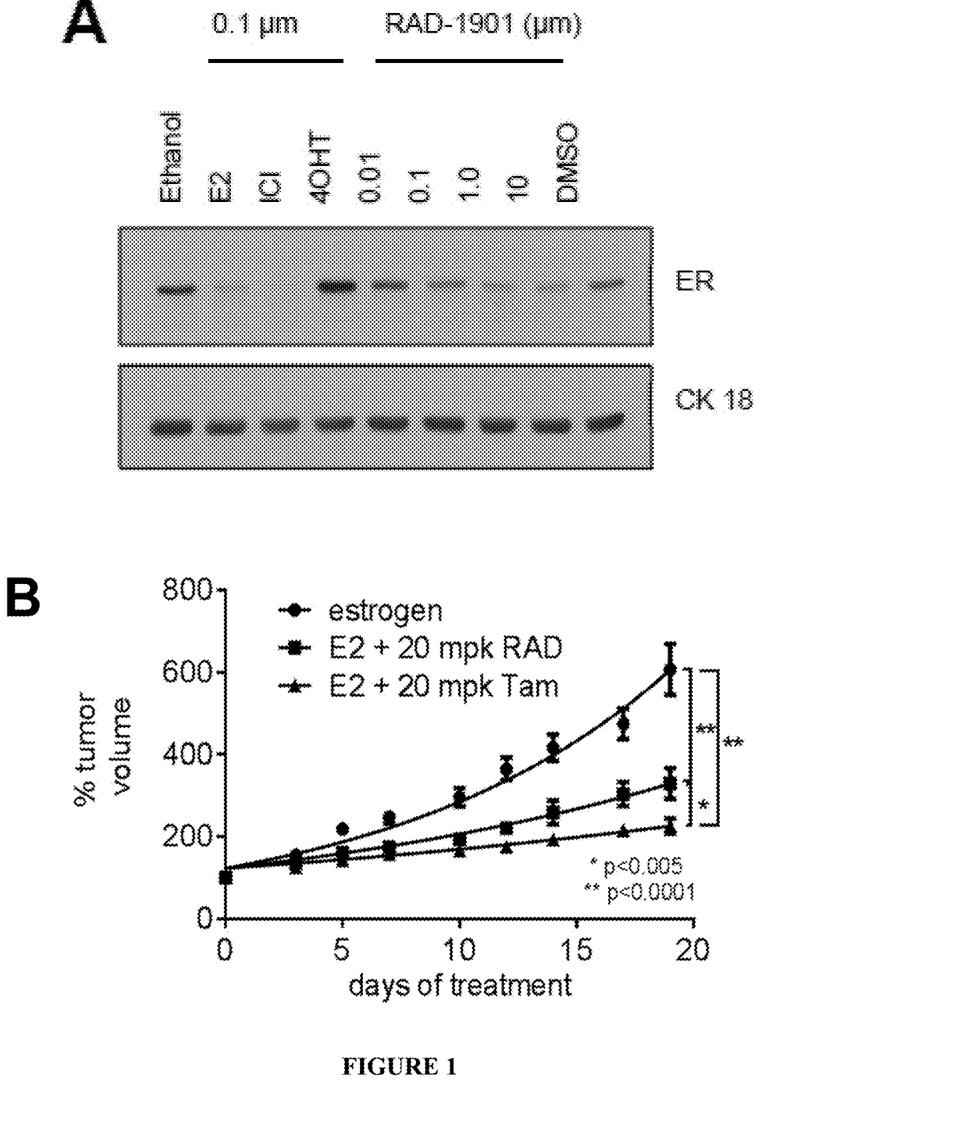
FIG. 1 shows treatment with (R)-6-{2-{ethyl[4-(2-ethylaminoethyl)benzyl]amino}-4-methoxyphenyl}-5,6,7,8-tetrahydronaphthalen-2-ol ("RAD 1901") results in a dose dependent reduction in ER expression and activity. A) MCF7 breast cancer cells were treated 4 hours as indicated prior to western blot detection of ER and loading control cytokeratin (CK) 18. B) Ovariectomized mice bearing MCF7 xenograft tumors were treated daily with RAD 1901 ("RAD") or tamoxifen ("Tam") in the context of continued estrogen treatment.

Turnover of ERα is significantly increased upon binding RAD1901, an activity that is more pronounced at higher drug concentrations (FIG. 1). This drug exhibits some of the characteristics that are generally attributed to selective estrogen receptor degraders (SERDs). Thus, at lower doses RAD1901 exhibits partial agonist activity, i.e., SERM activity, allowing for relief of hot flashes, but the SERD activity of the compound dominates when the receptor is exposed to higher concentrations. The present disclosure describes in vitro the mechanism by which RAD1901 impacts ER expression and investigates the possible result of such action in vivo.

As exemplified below, RAD 1901 surprisingly has the ability to degrade the estrogen receptor. Both in vitro and in vivo studies have since shown that the antagonist activity of this ligand correlates with estrogen receptor degradation in a dose dependent manner. RAD 1901 also inhibits estrogen dependent growth of breast cancer xenograft tumors and may be used to treat breast cancer, such as tamoxifen resistant breast cancer.

RAD 1901 is unique among both SERMs and SERDs in that this drug accumulates in the brain, an environment in which SERM penetration has been historically regarded as quite low. Estrogen receptor activity has been found to be important in the growth of tumors resistant to aromatase inhibitors and/or tamoxifen, and treatment with SERDs has been shown to have clinical benefit. While the revelation that RAD 1901 exhibits SERD activity certainly suggests potential utility in the treatment of progressing ER+ breast tumors, which was unappreciated prior to the present disclosure, the targeting of ER activity for the treatment of ER+ brain cancers represents a new frontier for the use of both SERMs and SERDs, as RAD 1901 represents the first SERM/SERD that can sufficiently penetrate the brain to exhibit efficacy. Because BCBM is generally diagnosed late in the disease progression of ER+ metastatic breast cancer, patients will in general have already been treated with endocrine therapeutics (i.e. tamoxifen or aromatase inhibitors). Thus, while SERMs such as tamoxifen have low brain penetration and have exhibited efficacy in anecdotal cases of BCBM that are detailed in the literature, the SERD activity of RAD 1901 becomes key to the therapeutic potential of this compound for treatment of BCBM, as SERDs have been found to be effective in breast cancers that are resistant to SERM or aromatase inhibitor therapy.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "administration" or "administering," as used herein refers to providing, contacting, and/or delivery of the SERM by any appropriate route to achieve the desired effect. These agents may be administered to a subject in numerous ways including, but not limited to, orally, ocularly, nasally, intravenously, topically, as aerosols, suppository, etc. and may be used in combination.

"Aromatase inhibitor" as used herein refers to a compound that targets aromatase, which is an enzyme involved in the biosynthesis of estrogen. Aromatase inhibitors may block the production of estrogen or block the action of estrogen on receptors.

"Blood brain barrier" or "BBB" as used herein refers to a highly selective permeability barrier that separates the circulating blood from the brain extracellular fluid in the central nervous system. The blood brain barrier may prevent the certain drugs from entering brain tissue and is a limiting factor in the delivery of many peripherally-administered agents to the central nervous system.

"Breast cancer" as used herein refers to a type of cancer that originates from and develops in the breast. "Metastatic breast cancer" refers to breast cancer that spreads outside the breast to the lymph nodes, bones, or other areas.

"Breast Cancer Brain Metastases" and "BCBM" as used interchangeably herein refer to breast cancer that has metastasized to the brain. BCBM may occur in up to 10-15% of breast-cancer patients. BCBM may progress rapidly and can produce life-threatening complications such as increased intracranial pressure, herniation of the brain and seizures.

Radiotherapy is a treatment of BCBM as it halts tumor progression quickly and can induce a response in the majority of patients.

"Cancer" as used herein refers to the uncontrolled and unregulated growth of abnormal cells in the body. Cancerous cells are also called malignant cells. Cancer may invade nearby parts of the body and may also spread to more distant parts of the body through the lymphatic system or bloodstream. Cancers include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

The term "effective dosage" as used herein means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, mammal, or human, such as reducing and/or inhibiting the function of the estrogen receptor. A therapeutically effective amount may be administered in one or more administrations (e.g., the agent may be given as a preventative treatment or therapeutically at any stage of disease progression, before or after symptoms, and the like), applications or dosages and is not intended to be limited to a particular formulation, combination or administration route. It is within the scope of the present disclosure that the SERM may be administered at various times during the course of treatment of the subject. The times of administration and dosages used will depend on several factors, such as the goal of treatment (e.g., treating v. preventing), condition of the subject, etc. and can be readily determined by one skilled in the art.

"Estrogen dependent cancer" or "estrogen receptor positive cancer" as used interchangeably herein refers to a tumor that contains estrogen receptor (ER) positive cells, i.e., cells that have estrogen receptors, and respond to the presence of estrogen with increased proliferation. Estrogen dependent cancers may include breast cancer, ovarian cancer, or endometrial cancer. "Estrogen receptor positive breast cancer" is a type of breast cancer that is sensitive to estrogen.

"Estrogen receptor" or "ER" as used interchangeably herein refers to a receptor that is activated by the hormone estrogen and is a member of the nuclear hormone family of intracellular receptors. There are two different isoforms of estrogen receptor, referred to as $\alpha$ (also referred to as "ERa") and $\beta$ (also referred to as "ERb"). ERa and ERb genes are encoded by ESR1 and ESR2 gene, respectively. Hormone-activated estrogen receptors form dimers and may form homodimers or heterodimers. Both ERs are widely expressed in different tissue types.

"Estrogen-receptor downregulators" as used herein refers to a drug or compound which binds and down-regulates the expression of an estrogen-receptor.

"Estrogen receptor negative breast cancer" or "Estrogen independent breast cancer" as used interchangeably herein refers to a tumor that does not contain estrogen receptor positive cells, i.e., cells that lack estrogen receptors, and does not depend on the presence of estrogen for ongoing proliferation.

"HER2 intervention drug" or "HER2 inhibitor" as used interchangeably herein refers to a compound that targets human Epidermal Growth Factor Receptor 2 (HER2). HER2 is a member of the epidermal growth factor receptor family and is involved in the development and progression of certain aggressive types of breast cancer, such as estrogen dependent breast cancer. A HER2 inhibitor may be a tyrosine kinase or a monoclonal antibody.

"Metastatic cancer" as used herein refers to a cancer that has spread from the part of the body where it started (the primary site) to other parts of the body.

"Progesterone receptor positive cancer" as used herein refers to a tumor that contains progesterone receptor positive (PR+) cells, i.e., cells that have progesterone receptors, which respond to the presence of progesterone with increased proliferation.

"Selective estrogen receptor degraders" or "SERDs" as used interchangeably herein refers to a compound that interacts with an ER and induce a conformational change that results in the degradation of the receptor.

"Selective estrogen receptor modulators" or "SERMs" as used interchangeably herein refers to a compound that interacts with an ER and whose relative agonist/antagonist activities are manifest in a cell selective manner. The prevention of estrogen binding to the estrogen receptor may lead to decreased proliferation of estrogen dependent cancer cells.

The term "subject", "patient" or "subject in the method" as used herein interchangeably, means any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject or subject may be a human or a non-human. In some embodiments, the subject may be a human subject at risk for developing or already suffering from cancer.

"Tamoxifen resistant breast cancer" as used herein refers to a breast cancer that does respond to treatment with tamoxifen.

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of the SERM to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

2. Methods of Treating Cancer with a SERM

The present invention is directed to methods of treating a subject suffering from cancer. The methods include administering a compound, i.e., SERM, having formula I:

(I)

wherein

TZ represents a C1-C4 alkylene group or —CR$^{f'}$R$^{g'}$—CH2-O— wherein R$^{f'}$ and R$^{g'}$ independently represent hydrogen or a C1-C6 alkyl group;

A represents a 5- to 14-membered heteroarylene group which may have a substituent or a C6-C14 arylene group which may have a substituent;

Y represents —CH$_2$—NR$^c$— wherein R$^c$ represents hydrogen or a C1-C6 alkyl group which may have a substituent; ring G represents the following formula:

R' represents 1 to 4 substituents independently selected from a hydrogen atom, a C1-C6 alkoxy group, and a hydroxyl group;

a partial structure in formula (I) represented by the following formula:

R" represents hydrogen, a hydroxyl group that may be further protected by a protecting group or a C1-C6 alkoxy group which may have a substituent; and R$^a$ and R$^b$ are the same as or different from each other and each represents a hydrogen atom, a C1-C6 alkyl group which may have a substituent, or a C3-C8 cycloalkyl group which may have a substituent, or when R$^a$ and R$^b$ are bonded together, they may form, together with the nitrogen atom that is adjacent to R$^a$ and R$^b$, a 4- to 10-membered single ring which may have a substituent; and L represents a single bond, or a salt thereof.

In certain embodiments, R$^a$ and R$^b$ independently may represent a hydrogen atom, a methyl group, an ethyl group, a n-propyl group, an iso-propyl group, a n-butyl group, an iso-butyl group, or a tert-butyl group. In certain embodiments, -T-Z— may represent —CH$_2$CH$_2$— or —C(CH$_3$)$_2$CH$_2$O—. In certain embodiments, Y may represent —CH2-N(CH$_2$CH$_3$)— or CH$_2$—N(CH$_2$CH$_2$OH)—. In certain embodiments, each of R" may independently represent a hydrogen atom or a methoxy group. In certain embodiments, R" may represent a hydroxyl group. In certain embodiments, A may represent a phenylene group. In certain embodiments, the compound may be (R)-6-{2-{ethyl[4-(2-ethylaminoethyl)benzyl]amino}-4-methoxyphenyl}-5,6,7,8-tetrahydronaphthalen-2-ol. Examples of other SERMS are described in U.S. Pat. No. 7,612,114, U.S. U.S. Pat. No. 7,960,412, U.S. Pat. No. 8,399,520, U.S. Patent Publication No. US 2009-0325930, and U.S. Patent Publication No. US 2006-0116364, the contents of which are incorporated by reference in their entirety. An effective amount of the compound may be administered.

(a) Dosages

In general, the dosage of administered SERM will vary depending upon such factors as the patient's age, weight, height, sex, general medical condition and previous medical history. Typically, it is desirable to provide the recipient with a dosage of SERM which is in the range of from about 1 pg/kg to 10 mg/kg (amount of agent/body weight of patient), although a lower or higher dosage also may be administered as circumstances dictate. Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of the SERM is a dose of between 0.1 and 200 mg/kg, for example between 0.1 and 10 mg/kg, or about 20 mg/kg to about 100 mg/kg. The therapeutically or prophylactically effective amount of the SERM may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated.

In some embodiments, the SERM can be administered to a patient in an amount of about 10 mg/day to about 500 mg/day, about 10 mg/day to about 200 mg/day (e.g., 10, 20, 30, 40, 50, 60, 70, 80, 90, 100, 110, 120, 130, 140, 150, 160, 170, 180, 190, or 200 mg/day), 20 mg/day to about 100 mg/day, 100 mg/day to about 200 mg/day, or about 200 mg/day to about 500 mg/day (e.g., 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 mg/day), inclusive of any single or multi-dose daily administration regimen that falls within that total daily dose range. In some embodiments, the dose is from about 20 mg/day to about 100 mg/day. Additionally, one of ordinary skill in the art would also know how to adjust or modify variables such as dosage, dosage schedules, and routes of administration, as appropriate, for a given subject.

Further, the SERM dose may be determined by a person skilled in the art and may vary according to factors such as the disease state, age, sex, and weight of the individual, and the ability of the SERM to elicit a desired response in the individual. The dose is also one in which toxic or detrimental effects, if any, of the SERM are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

(b) Rad 1901

The SERM may be RAD 1901. Although RAD 1901 may effectively treat vasomotor symptoms, its pharmacology is complex. Treatment of ER positive breast cancer cells with RAD 1901 in MCF7 and BT483 cells resulted in a pronounced dose dependent down regulation of the receptor expression. RAD 1901 is a unique SERM in that it apparently has a relative agonist/antagonist activity in the brain that is determined by dose. At low doses RAD 1901, behaves as a SERM as it exhibits estrogenic activity. At high doses, RAD 1901 may function as a SERD, reversing the response.

While targeting of the estrogen signaling axis has proven effective in the treatment of breast cancer and osteoporosis, implementing a safe therapy that mitigates the vasomotor. While efforts are being made to address this unmet medical need using tissue specific estrogen complexes (TSECs) that combine estrogens and SERMs with the intention of inhibiting estrogen action only in some tissues (i.e. breast and uterus), preliminary clinical data suggest that RAD 1901 may accomplish the same medical goal without exposing the patient to estrogen. The apparent dose dependent down regulation of ER by RAD1901 suggest that at a therapeutic (low) dose, RAD1901 may be mediating some level of agonist activity, while a higher dose results in more extensive SERM activity and an effective blockade in estrogen signaling, thereby exacerbating vasomotor symptoms.

In some embodiments, a low dose of RAD 1901 may be about 0 mg/kg to about 25 mg/kg, about 0 mg/kg to about 20 mg/kg, about 0 mg/kg to about 15 mg/kg, about 0 mg/kg to about 10 mg/kg, about 0 mg/kg to about 5 mg/kg, about 1 mg/kg to about 25 mg/kg, about 1 mg/kg to about 20 mg/kg, about 1 mg/kg to about 15 mg/kg, about 1 mg/kg to about 10 mg/kg, about 1 mg/kg to about 5 mg/kg, about 2 mg/kg to about 25 mg/kg, about 2 mg/kg to about 20 mg/kg, about 2 mg/kg to about 15 mg/kg, about 2 mg/kg to about 10 mg/kg, about 2 mg/kg to about 5 mg/kg, about 3 mg/kg to about 25 mg/kg, about 3 mg/kg to about 20 mg/kg, about 3 mg/kg to about 15 mg/kg, about 3 mg/kg to about 10 mg/kg, about 3 mg/kg to about 5 mg/kg, about 4 mg/kg to about 25 mg/kg, about 4 mg/kg to about 20 mg/kg, about 4 mg/kg to about 15 mg/kg, about 4 mg/kg to about 10 mg/kg, about 4 mg/kg to about 5 mg/kg, about 5 mg/kg to about 25 mg/kg, about 5 mg/kg to about 20 mg/kg, about 5 mg/kg to about 15 mg/kg, about 5 mg/kg to about 10 mg/kg, about 5 mg/kg to about 7.5 mg/kg. In some embodiments, a low dose of RAD 1901 may be less than about 25 mg/kg, about 24 mg/kg, about 23 mg/kg, about 22 mg/kg, about 21 mg/kg, about 20 mg/kg, about 19 mg/kg, about 18 mg/kg, about 17 mg/kg, about 16 mg/kg, about 15 mg/kg, about 14 mg/kg, about 13 mg/kg, about 12 mg/kg, about 11 mg/kg, about 10 mg/kg, about 9 mg/kg, about 8 mg/kg, about 7 mg/kg, about 6 mg/kg, about 5 mg/kg, about 4 mg/kg, about 3 mg/kg, about 2 mg/kg, or about 1 mg/kg.

In some embodiments, a high dose of RAD 1901 may be about 15 mg/kg to about 500 mg/kg, about 15 mg/kg to about 250 mg/kg, about 15 mg/kg to about 200 mg/kg, about 15 mg/kg to about 150 mg/kg, about 15 mg/kg to about 100 mg/kg, about 15 mg/kg to about 75 mg/kg, about 20 mg/kg to about 500 mg/kg, about 20 mg/kg to about 250 mg/kg, about 20 mg/kg to about 200 mg/kg, about 20 mg/kg to about 150 mg/kg, about 20 mg/kg to about 100 mg/kg, about 20 mg/kg to about 75 mg/kg, about 25 mg/kg to about 500 mg/kg, about 25 mg/kg to about 250 mg/kg, about 25 mg/kg to about 200 mg/kg, about 25 mg/kg to about 150 mg/kg, about 25 mg/kg to about 100 mg/kg, or about 25 mg/kg to about 75 mg/kg. In some embodiments, a high dose of RAD 1901 may be more than about 15 mg/kg, 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 105 mg/kg, about 110 mg/kg, about 115 mg/kg, about 120 mg/kg, about 125 mg/kg, about 130 mg/kg, about 135 mg/kg, about 140 mg/kg, about 145 mg/kg, about 150 mg/kg, about 155 mg/kg, about 160 mg/kg, about 165 mg/kg, about 170 mg/kg, about 175 mg/kg, about 180 mg/kg, about 185 mg/kg, about 190 mg/kg, about 195 mg/kg, about 200 mg/kg, about 250 mg/kg, about 300 mg/kg, about 350 mg/kg, about 400 mg/kg, about 450 mg/kg or about 500 mg/kg.

In some embodiments, RAD1901 can be administered to a patient in an amount of about 10 mg/day to about 500 mg/day, about 10 mg/day to about 200 mg/day (e.g., 10, 20, 30, 40, 50, 60, 70, 80, 90, 100, 110, 120, 130, 140, 150, 160, 170, 180, 190, or 200 mg/day), 20 mg/day to about 100 mg/day, 100 mg/day to about 200 mg/day, or about 200 mg/day to about 500 mg/day (e.g., 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 mg/day), inclusive of any single or multi-dose daily administration regimen that falls within that total daily dose range. In some embodiments, the dose is from about 20 mg/day to about 100 mg/day. Additionally, one of ordinary skill in the art would also know how to adjust or modify variables such as dosage, dosage schedules, and routes of administration, as appropriate, for a given subject.

3. Methods of Treating Estrogen Receptor Positive Cancer of the Brain

The methods described above may be used to treat an estrogen receptor positive cancer of the brain. In some embodiments, the cancer may include subtypes of brain tumors that may express ER, such as Breast Cancer Brain Metastases (BCBM), Astrocytoma, Chondrosarcoma, Craniopharyngioma, Glioblastoma, Glioma, Hemangioma, Medulloblastoma, Meningioma, Neurofibroma, Neuronal and Mixed Neuronal-Glial Tumors, Oligoastrocytoma, Pituitary Tumor, PNET—(primitive neuroectodermal tumor), Schwannomak, or Leptomeningeal metastases. In some embodiments, the cancer may be other cancers such as Atypical Teratoid Rhabdoid Tumor (ATRT), Choroid Plexus Carcinoma, Ependymoma, Germ Cell Tumor, Juvenile Pilocytic Astrocytoma, Oligodendroglioma, or Pineal Tumor.

(a) Breast Cancer Brain Metastases

The methods described above may be used to treat a subject suffering from breast cancer brain metastases. 10-20% of breast cancer patients ultimately experience breast cancer metastasis to the brain, i.e., BCBM. 30-40% of BCBM express ER. ER expression is retained in 50-65% of BCBM that arise from ER+/PR+ tumors, despite treatment of the initial tumor with endocrine therapies. As many as 50% of BCBM express the estrogen receptor, and the brain is an environment rich in aromatase activity, suggesting that estrogen levels and signaling may be of importance in the establishment and maintenance of BCBM. Therefore, the availability of the SERM, such as RAD 1901 or a similar SERM with significant brain penetrance, that can induce estrogen receptor turnover in BCBM may provide therapeutic benefit in the treatment of BCBM.

(b) Astrocytoma

Astrocytoma is a type of cancer of the brain that originate in astrocytes, which are a particular kind of glial cells, start-shaped brains cells in the cerebrum. Low ERb expression has been shown to be associated with the progression of astrocytoma.

(c) Chondrosarcoma

Chondrosarcoma is a type of tumor that affects the bones and joints. Chondrosarcoma grow from the types of cells that make cartilage in the skull. In the head, these tumors grow inside the bones at the base of the back part of the skull and may be very close to the nerves and blood vessels around the brainstem. ER is present and active in chondrosarcoma tumors.

(d) Craniopharyngioma

Craniopharyngioma is a benign tumor that develops near the pituitary gland. ER may be present in craniopharyngioma and may be associated with improved disease prognosis.

(e) Glioblastoma Multiforme

Glioblastoma multiforme, also known as "glioblastoma," is the most common and most aggressive malignant primary brain tumor in humans, involving glial cells and accounting for 52% of all functional tissue brain tumor cases and 20% of all intracranial tumors. Glioblastoma may express both ERs, which may play a role in etiology and treatment.

(f) Glioma

Glioma is a type of tumor that starts in the brain or spine and arises from glial cells. Gliomas make up approximately 30% of all brain and central nervous system tumors and 80% of all malignant brain tumors. Glioma may express both ERs, which may play a role in etiology and treatment. Glioma may be responsive to tamoxifen treatment.

(g) Hemangioma

Hemangioma is a benign and usually self-involuting tumor (swelling or growth) of the endothelial cells that line blood vessels. Hemangioma is characterized by increased number of normal or abnormal vessels filled with blood. Human vascular endothelial cells express ER isoforms and are responsive to tamoxifen treatment. Hemangioma may be intracranial hemangiomas or cutaneous hemangiomas.

(h) Medulloblastoma

Medulloblastoma is a highly malignant primary brain tumor that originates in the cerebellum or posterior fossa. Medulloblastomas may originate from immature or embryonal cells at their earliest stage of development. Medulloblastoma may express ER isoforms. ER isoforms are associated with growth and migration of these cells.

(i) Meningioma

Meningiomas are a diverse set of tumors arising from the meninges, i.e., the membranous layers surrounding the central nervous system. Meningioma may express both ER isoforms. Meningioma may be responsive to tamoxifen treatment.

(j) Neurofibroma

Neurofibroma is a benign nerve sheath tumor in the peripheral nervous system. Neurofibromas arise from non-myelinating-type Schwann cells that exhibit biallelic inactivation of the NF1 gene that codes for the protein neurofibromin. Neurofibroma may be ER positive.

(k) Neuronal & Mixed Neuronal-Glial Tumors

Neuronal & Mixed Neuronal-Glial Tumors are rare, benign tumors that come from ganglion-type cells, i.e., groups of nerve cells. ER may be present in these tumors.

(l) Oligoastrocytoma

Oligoastrocytomas are a subset of brain tumors that present with an appearance of mixed glial cell origin, astrocytoma and oligodendroglioma. Oligoastrocytoma may have a lasting response to tamoxifen treatment.

(m) Pituitary Tumor

A pituitary tumor is an abnormal growth in the pituitary gland. Both ERa and ERb may be detected in pituitary tumors.

(n) Primitive neuroestodermal tumor (PNET)

Primitive neuroestodermal tumor is a neural crest tumor. The majority of the cells in the PNET are derived from neuroectoderm, but have not developed and differentiated in the way a normal neuron would, and so the cells appear "primitive. ERa may be present and may increase metastatic potential via extracellular signal-regulated Kinase (ERK) activation.

(o) Schwannoma

Schwannoma (also known as an "neurilemmoma," "neurinoma," "neurolemmoma," and "Schwann cell tumor") is a benign nerve sheath tumor composed of Schwann cells, which normally produce the insulating myelin sheath covering peripheral nerves. Schwannoma may express ERα.

(p) Leptomeningeal Metastases

Leptomeningeal metastases is breast cancer metastasis to the membranes (meninges) surrounding the brain and spinal cord. A durable response has been observed in patient(s) treated with aromatase inhibitors, which suggests possible responsiveness to ER targeted therapies.

4. Methods of Treating a Cancer that is Resistant to an Estrogen Receptor Modulator The methods described above may be used to treat a cancer that is resistant to an estrogen receptor modulator. The resistance to the estrogen receptor modulator may be acquired. The estrogen receptor modulator may be a selective estrogen receptor modulator (SERM). The SERM may be tamoxifen, idoxifene, raloxifene or ICI 182,780. The cancer may be breast, endometrial or ovarian cancer. The cancer may be tamoxifen resistant breast cancer.

5. Mechanisms of Delivery

The SERM may be formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the SERM is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Various delivery systems are known and can be used to administer one or more SERMs or the combination of one or more SERMs and a prophylactic agent or therapeutic agent useful for preventing, managing, treating, or ameliorating a disorder or one or more symptoms thereof, e.g., encapsulation in liposomes, microparticles, microcapsules, receptor-mediated endocytosis (see, e.g., Wu and Wu, J. Biol. Chem. 262:4429-4432 (1987)), etc. Methods of administering a prophylactic or therapeutic agent of the SERM include, but are not limited to, parenteral administration (e.g., intradermal, intramuscular, intraperitoneal, intravenous and subcutaneous), epidural administration, intratumoral administration, and mucosal administration (e.g., intranasal and oral routes).

6. Combination Treatments

The methods described above may include a combination treatment of the compound of formula I with other drugs and/or other conventional cancer therapies, such as hormone therapy.

(a) Combination Drugs

The methods may further include administering an effective amount of at least one compound of a cyclin-dependent kinase 4 and 6 inhibitor (CDK4/6 inhibitor), an antiestrogen, a ligand of retinoic acid or retinoic X receptor, an antiprogestin, an antiandrogen, vitamin D or metabolite thereof, a farnesyl transferase inhibitor, a PPARα or gamma agonist and a MAP kinase inhibitor.

(b) Conventional Cancer Therapies

Conventional cancer therapies may include surgery, radiation therapy, chemotherapy, hormone therapy, and targeted therapy. Examples of surgery include open craniotomy with maximal excision, which may be followed by radiation therapy. Examples of radiation therapy include whole-brain irradiation, fractionated radiotherapy, and radiosurgery, such as stereotactic radiosurgery, e.g., Gamma Knife radiosurgery. Examples of chemotherapy include anthracyclines, such as doxorubicin (Adriamycin, Doxil), epirubicin (Ellence), and daunorubicin (Cerubidine, DaunoXome), capecitabine (Xeloda), carboplatin (Paraplatin), cisplatin, cyclophosphamide (Cytoxan), eribulin (Halaven), fluorouracil (also called 5-fluorouracil or 5-FU; Adrucil), gemcitabine (Gemzar), ixabepilone (Ixempra), methotrexate (Amethopterin, Mexate, Folex), mitoxantrone (Novantrone), mutamycin (Mitomycin), taxanes, such as paclitaxel (Taxol, Abraxane), and docetaxel (Taxotere), thiotepa (Thioplex), vincristine (Oncovin, Vincasar PES, Vincrex), and vinorelbine (Navelbine). Examples of targeted therapy include trastuzumab (Herceptin), lapatinib (Tykerb), bevacizumab (Avastin), pertuzumab (Perjeta), and everolimus (Afinitor).

i. Endocrine Therapy (Hormone Therapy)

Endocrine therapy, also known as hormonal therapy, hormone therapy, and hormone treatment, is a treatment that adds, blocks, or removes hormones. For example, hormones may be given to adjust low hormone levels. Synthetic hormones or other drugs may be given to block the body's natural hormones to slow or stop the growth of certain cancers (such as prostate and breast cancer). Endocrine therapy may also include surgery to remove the gland that makes a certain hormones.

Examples of hormone therapy include selective estrogen receptor modulators (SERMs), such as tamoxifen, raloxifene, endoxifene, toremifene, lasofoxifene, pipendoxifene, bazedoxifene, and ospemifene, aromatase inhibitors, such anastrozole, letrozole, exemestane, formestane, fadrozole, aminoglutethimide, and testolactone, a HER2 intervention drug, such as a HER2 inhibitor, such as Herceptin (trastuzumab), pertuzumab, and lapatinib, and estrogen-receptor downregulators, such as fulvestrant (ICI 182,780).

7. Subject or Subject in the Method

The methods described above are directed to treating a subject with a SERM. The subject treated by the methods described above may be a subject or patient suffering from or at risk of suffering from an estrogen receptor positive cancer of the brain, such as BCBM, or a cancer that is resistant to an estrogen receptor modulator, such as tamoxifen resistant breast cancer. The subject may be diagnosed or identified as having or at risk of having cancer using known methods and assays, such as a biopsy. The subject may be treated with SERM alone or in combination with another drug and/or conventional cancer therapy, as described above. The subject may be treated with the SERM as a neoadjuvant therapy or post-surgery. The present invention has multiple aspects, illustrated by the following non-limiting examples.

8. Examples

The foregoing may be better understood by reference to the following examples, which are presented for purposes of illustration and are not intended to limit the scope of the invention.

Example 1

In Vitro Analysis of ER Degradation 48 hours prior to treatment, MCF7 cells were plated in phenol red free DMEM/F12 media supplemented with 8% charcoal stripped fetal bovine serum, non-essential amino acids, and sodium pyruvate. After 20 hours of treatment with the indicated ligands, i.e., estradiol ("E2"; Sigma-Aldrich), antiestrogen ICI 182,780 ("ICI"; Sigma-Aldrich), and 4-hydroxytamoxifen ("4OHT"; Sigma-Aldrich), (0-1 µM), cells were washed and lysed in RIPA lysis buffer (50 mM Tris, pH 8, 150 mM NaCl, 1% IGEPAL, 0.02% SDS, 0.5% sodium deoxycholate, 1 mM EDTA). 50 ug of cleared lysate was resolved by SDS-PAGE and analyzed by immunoblot detection of ERα or cytokeratin 18 (loading control), as illustrated in FIG. 1A.

Example 2

In Vivo Analysis of RAD 1901 in MCF7 Xenograft Tumors

A total of 90 female Nu/Nu mice were ovariectomized and implanted subcutaneous simultaneously with an estrogen pellet (Innovative Research of America) releasing 0.72 mg estradiol (E2) over 60 days. 2 days later an approximately 6 mm$^3$ fragment of an MCF7 xenograft tumor (isolated from a recently sacrificed estrogen treated nu/nu mouse) was inserted subcutaneous into the axial mammary gland. Tumor growth (by caliper measurement) and animal body weight were monitored 3× weekly until tumor volume reached ~0.2 cm$^3$. Mice (n~10) were randomized to the following groups: estrogen control (corn oil vehicle), E2+RAD 1901 (20 mg/kg; Radius Health, Inc.), E2+Tamoxifen (20 mg/kg; Sigma-Aldrich). Treatments were formulated in sterile corn oil and were administered daily by subcutaneous injection. After 3 weeks of treatments, animals were euthanized and serum and tissues saved for analysis. FIG. 1B depicts tumor volume analyzed using non-linear curve fit and exponential growth calculation (Graphpad Prism), followed by two-way ANOVA and Bonferroni analysis.

Example 3

Mechanism by which RAD1901 Downregulates ER Expression

Figure 2:
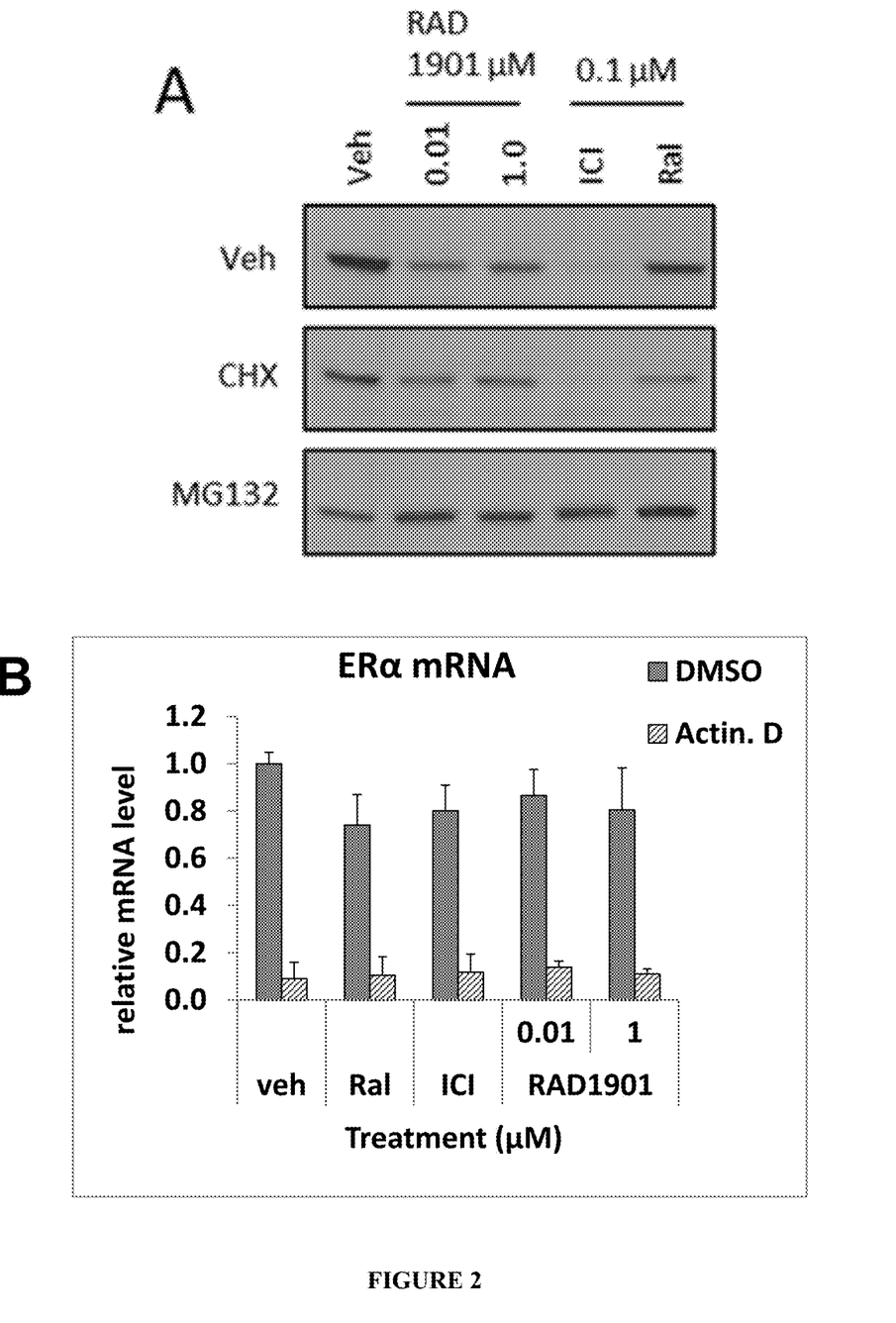
FIG. 2 shows RAD1901 downregulates ERα expression.

While the reduced levels of ER following treatment with RAD 1901 results in receptor degradation, whether the drug influences the transcriptional activity of the gene encoding ER was determined. (FIG. 2) MCF7 cells were pre-treated with Vehicle (Veh) or translation (cyclohexamide—CHX, 10 µg/ml), proteasome (MG132, 30 µM) or transcription (Actinomycin D—Actin. D, 100 ng/ml) inhibitors for 2 hours prior to 6 hours of treatment with RAD 1901 (0.1 or 1 µM), or 0.1 µM ICI 182,780 (ICI) or raloxifene (Ral). FIG. 2A shows ERα protein expression in whole cell extracts was analyzed by immunoblot, as in Example 1. FIG. 2B shows cells treated, as indicated, were washed in PBS prior to lysis. RNA isolation (BioRad) and reverse transcription (iScript; BioRad) were performed per kit manufacturer's instructions. qRT-PCR of cDNA was done using iQ SYBR Green Supermix (Bio-Rad) per kit instructions and performed using the iCycler optical system with associated software (Bio-Rad). mRNA abundance was calculated using the ΔΔCT method to normalize ERα mRNA expression to similarly detected housekeeping gene 36B4.

Example 4

Conformational Changes Induced in ER as a Consequence of Binding of RAD1901

A series of short peptides whose ability to interact with ERα is influenced by the nature of the bound ligand were previously identified (see Chang et al. Methods Enzymol. (2003) 364:118-42; Huang et al. Mol Endocrinol. (2002) 16(8):1778-92; Connor et al. Cancer Res. (2001) 61(7): 2917-22; Chang et al. Mol Cell Biol. (1999) 19(12):8226-39; and Norris et al. Science (1999) 285(5428):744-6). The interaction of these "conformational probes" can be measured in vitro or within intact cells and thus enables the definition of ligand induced conformational changes in the receptor. This is significant, since differences in receptor conformation facilitate the engagement of different coregulatory proteins resulting in different pharmacological activities. Application of this technology has led to the determination that their impact on receptor structure is a distinguishing feature of ER ligands.

Figure 3:
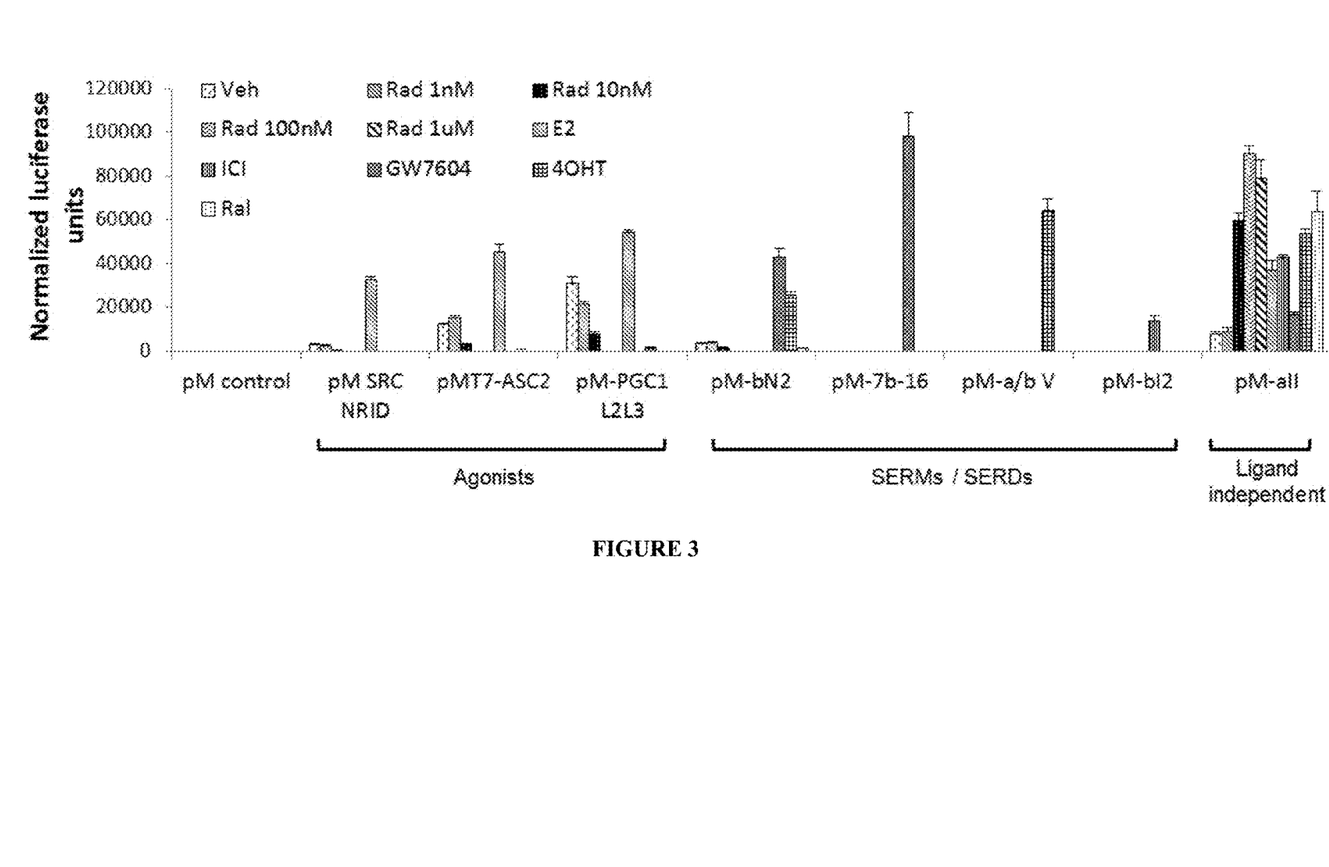
FIG. 3 shows the interaction between ER and conformation-specific peptides in mammalian two-hybrid system.

FIG. 3 shows that Rad 1901 induces a unique conformation of ERα as shown in the interaction between ER and conformation-specific peptides in a mammalian two-hybrid system. Triplicate wells of SKBR3 cells were transfected (Lipofectin per manufacturer's instructions) with plasmids expressing ERα fused to VP 16 together with Gal4DBD alone (control) or fused to ER interacting peptides noted on the horizontal axis. Cells were then treated with Rad 1901 (1 nM-1 µM) or the indicated ER ligands (100 nM). Interaction of ERα with the Gal4DBD peptide constructs was detected through activation of a Gal4 responsive luciferase reporter construct and was normalized to detected β-galactosidase activity generated by a co-transfected constitutive expression vector. Ligand classes recognized by each probe are indicated below the graph.

Example 5

RAD1901 Possesses Dose Dependent Agonist and/or Antagonist Potential

Figure 4:
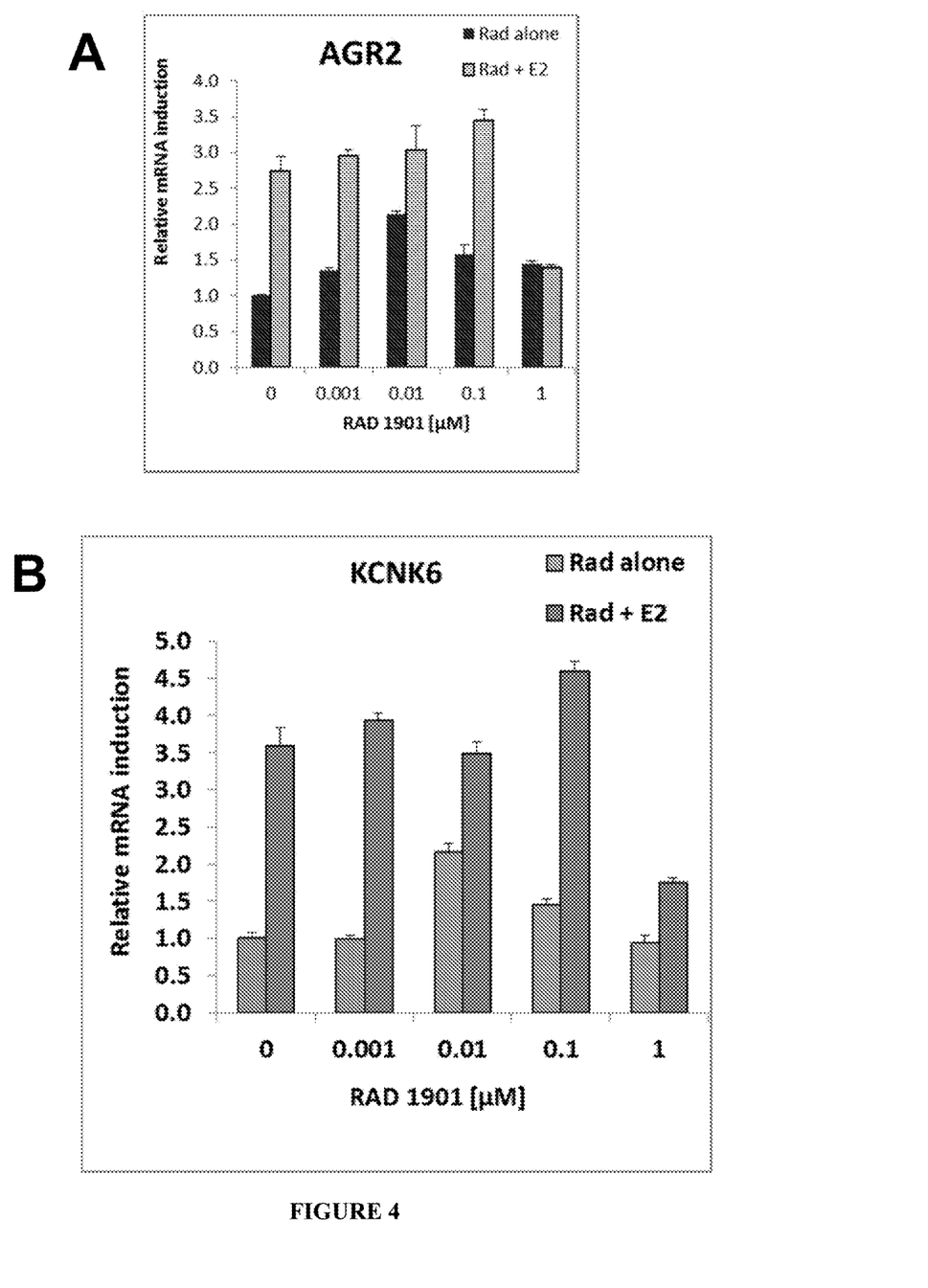
FIG. 4 shows RAD 1901 exhibits dose dependent agonist/antagonist regulation of ER target genes.

The complex pharmacological activities exhibited by RAD 1901 suggest that it will exhibit a unique gene expression profile in target cells. A recent extensive microarray analysis has identified "sentinel" subsets of ER-responsive genes that can differentiate between ER agonists, SERMs and SERDs. For example, some of these are responsive to only the SERM tamoxifen, while others display a graded response to SERMs with varying agonist/antagonist potential, and yet others are repressed by agonists or SERMs and are induced only by SERDs. RAD 1901 exhibits dose dependent agonist/antagonist regulation of ER transactivation of target genes (FIG. 4). MCF7 breast cancer cells were treated 24 hours with RAD 1901 (0-1 µM) in the presence or absence of 17β-estradiol (1 nM). RNA isolation and the analysis of the expression of target genes Anterior gradient protein 2 (AGR2) and KCNK6 was conducted as in Example 3.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A method of treating estrogen receptor positive cancers of the brain in a subject, the method comprising administering a compound represented by the following formula I:

wherein

TZ represents a C1-C4 alkylene group or —CR$^f$R$^{g'}$—CH2-O— wherein R$^f$ and R$^{g'}$ independently represent hydrogen or a C1-C6 alkyl group;

A represents a 5- to 14-membered heteroarylene group which may have a substituent or a C6-C14 arylene group which may have a substituent;

Y represents —CH$_2$—NR$^c$— wherein R$^c$ represents hydrogen or a C1-C6 alkyl group which may have a substituent;

ring G represents the following formula:

R' represents 1 to 4 substituents independently selected from a hydrogen atom, a C1-C6 alkoxy group, and a hydroxyl group;

a partial structure in formula (I) represented by the following formula:

R" represents hydrogen, a hydroxyl group that may be further protected by a protecting group or a C1-C6 alkoxy group which may have a substituent; and

R$^a$ and R$^b$ are the same as or different from each other and each represents a hydrogen atom, a C1-C6 alkyl group which may have a substituent, or a C3-C8 cycloalkyl group which may have a substituent, or when R$^a$ and R$^b$ are bonded together, they may form, together with the nitrogen atom that is adjacent to R$^a$ and R$^b$, a 4- to 10-membered single ring which may have a substituent; and L represents a single bond, or a salt thereof.

Clause 2. The method of clause 1, wherein the cancer is Breast cancer brain metastases, Astrocytoma, Atypical Teratoid Rhabdoid Tumor (ATRT), Chondrosarcoma, Choroid Plexus Carcinoma, Craniopharyngioma, Ependymoma, Germ Cell Tumor, Glioblastoma, Glioma, Hemangioma, Juvenile Pilocytic Astrocytoma, Medulloblastoma, Meningioma, Neurofibroma, Neuronal and Mixed Neuronal-Glial Tumors, Oligoastrocytoma, Oligodendroglioma, Pineal Tumor, Pituitary Tumor, PNET—(primitive neuroectodermal tumor), Schwannoma, and Leptomeningeal metastases.

Clause 3. A method of treating breast cancer brain metastasis in a subject, the method comprising administering a compound represented by the following formula I:

wherein

TZ represents a C1-C4 alkylene group or —CR$^f$R$^{g'}$—CH2-O— wherein R$^f$ and R$^{g'}$ independently represent hydrogen or a C1-C6 alkyl group;

A represents a 5- to 14-membered heteroarylene group which may have a substituent or a C6-C14 arylene group which may have a substituent;

Y represents —CH$_2$—NR$^c$— wherein R$^c$ represents hydrogen or a C1-C6 alkyl group which may have a substituent;

ring G represents the following formula:

R' represents 1 to 4 substituents independently selected from a hydrogen atom, a C1-C6 alkoxy group, and a hydroxyl group;

a partial structure in formula (I) represented by the following formula:

R" represents hydrogen, a hydroxyl group that may be further protected by a protecting group or a C1-C6 alkoxy group which may have a substituent; and $R^a$ and $R^b$ are the same as or different from each other and each represents a hydrogen atom, a C1-C6 alkyl group which may have a substituent, or a C3-C8 cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and L represents a single bond, or a salt thereof.

Clause 4. A method of treating a cancer in a subject, wherein the cancer is resistant to an estrogen receptor modulator, the method comprising administering a compound represented by the following formula I:

(I)

wherein

TZ represents a C1-C4 alkylene group or —$CR^{f'}R^{g'}$—CH2-O— wherein $R^{f'}$ and $R^{g'}$ independently represent hydrogen or a C1-C6 alkyl group;

A represents a 5- to 14-membered heteroarylene group which may have a substituent or a C6-C14 arylene group which may have a substituent;

Y represents —$CH_2$—$NR^c$— wherein $R^c$ represents hydrogen or a C1-C6 alkyl group which may have a substituent;

ring G represents the following formula:

R' represents 1 to 4 substituents independently selected from a hydrogen atom, a C1-C6 alkoxy group, and a hydroxyl group;

a partial structure in formula (I) represented by the following formula:

R" represents hydrogen, a hydroxyl group that may be further protected by a protecting group or a C1-C6 alkoxy group which may have a substituent; and $R^a$ and $R^b$ are the same as or different from each other and each represents a hydrogen atom, a C1-C6 alkyl group which may have a substituent, or a C3-C8 cycloalkyl group which may have a substituent, or when $R^a$ and $R^b$ are bonded together, they may form, together with the nitrogen atom that is adjacent to $R^a$ and $R^b$, a 4- to 10-membered single ring which may have a substituent; and L represents a single bond, or a salt thereof.

Clause 5. The method of clause 4, wherein the cancer is de novo resistant to the estrogen receptor modulator.

Clause 6. The method of clause 4, wherein the resistance to the estrogen receptor modulator is acquired.

Clause 7. The method of clause 4, wherein the estrogen receptor modulator is a selective estrogen receptor modulator (SERM).

Clause 8. The method of clause 7, wherein the SERM is tamoxifen, idoxifene, raloxifene or ICI 182,780.

Clause 9. The method of any one of clauses 4-8, wherein the cancer is breast, endometrial or ovarian cancer.

Clause 10. The method of any one of clauses 4-9, wherein the cancer is breast cancer.

Clause 11. The method of any one of clauses 1-10, wherein $R^a$ and $R^b$ independently represent a hydrogen atom, a methyl group, an ethyl group, a n-propyl group, an iso-propyl group, a n-butyl group, an iso-butyl group, or a tert-butyl group.

Clause 12. The method of any one of clauses 1-10, wherein -T-Z— represents $CH_2CH_2$— or —$C(CH_3)_2CH_2O$—.

Clause 13. The method of any one of clauses 1-10, wherein Y represents —CH2-N($CH_2CH_3$)— or —$CH_2$—N($CH_2CH_2OH$)—.

Clause 14. The method of any one of clauses 1-10, wherein each of R" independently represents a hydrogen atom or a methoxy group.

Clause 15. The method of any one of clauses 1-10, wherein R" represents a hydroxyl group.

Clause 16. The method of any one of clauses 1-10, wherein A represents a phenylene group.

Clause 17. The method of any one of clauses 1-10, wherein the compound is (R)-6-{2-{ethyl[4-(2-ethylaminoethyl)benzyl]amino}-4-methoxyphenyl}-5,6,7,8-tetrahydronaphthalen-2-ol.

Clause 18. The method of any one of clauses 1-10, wherein an effective amount of the compound is administered.

Clause 19. The method of any one of clauses 1-10, wherein the effective amount comprises a high dosage.

Clause 20. The method of clause 19, wherein the high dosage is more than about 20 mg/kg.

Clause 21. The method of clause 19 or 20, wherein the high dosage is about 20 mg/kg to about 100 mg/kg.

Clause 22. The method of any one of clauses 1-10, wherein the compound is administered by oral administration, intravenous administration, intradermal injection, intramuscular injection or subcutaneous injection.

Clause 23. The method of any one of clauses 1-10, further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

What is claimed is:

1. A method of treating breast cancer brain metastasis in a subject, the method comprising administering a compound of (R)-6-{2-{ethyl[4-(2-ethylaminoethyl)benzyl]amino}-4-methoxyphenyl}-5,6,7,8-tetrahydronaphthalen-2-ol, wherein the breast cancer brain metastasis is resistant to an estrogen receptor modulator.

2. The method of claim 1, wherein an effective amount of the compound is administered.

3. The method of claim 2, wherein the effective amount comprises a high dosage.

4. The method of claim 3, wherein the high dosage is more than about 20 mg/kg.

5. The method of claim 3, wherein the high dosage is about 20 mg/kg to about 100 mg/kg.

6. The method of claim 1, wherein the compound is administered by oral administration, intravenous administration, intradermal injection, intramuscular injection or subcutaneous injection.

7. The method of claim 1, further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

8. The method of claim 1, wherein the breast cancer brain metastasis is de novo resistant to the estrogen receptor modulator.

9. The method of claim 1, wherein the resistance to the estrogen receptor modulator is acquired.

10. The method of claim 1, wherein the estrogen receptor modulator is a selective estrogen receptor modulator (SERM).

11. The method of claim 10, wherein the SERM is tamoxifen, idoxifene, raloxifene or ICI 182,780.

12. The method of claim 1, wherein the estrogen receptor modulator is an aromatase inhibitor.

13. The method of claim 12, wherein the aromatase inhibitor is anastrozole, letrozole or exemestane.

14. A method of treating breast cancer brain metastasis in a subject, the method comprising administering a composition comprising (R)-6-{2-{ethyl[4-(2-ethylaminoethyl)benzyl]amino}-4-methoxyphenyl}-5,6,7,8-tetrahydronaphthalen-2-ol, wherein the breast cancer brain metastasis is resistant to an estrogen receptor modulator.

15. The method of claim 14, wherein the breast cancer brain metastasis is estrogen receptor positive.

16. The method of claim 14, wherein an effective amount of the composition is administered.

17. The method of claim 16, wherein the effective amount comprises a high dosage.

18. The method of claim 17, wherein the high dosage is more than about 20 mg/kg.

19. The method of claim 17, wherein the high dosage is about 20 mg/kg to about 100 mg/kg.

20. The method of claim 14, wherein the composition is administered by oral administration, intravenous administration, intradermal injection, intramuscular injection or subcutaneous injection.

21. The method of claim 14, further comprising administering an effective amount of at least one compound selected from the group consisting of a cyclin-dependent kinase 4 and 6 inhibitor (CDK4/6 inhibitor), an antiestrogen, a ligand of retinoic acid or retinoxic X receptor, an antiprogestin, an antiandrogen, vitamin D or metabolite thereof, a farnesyl transferase inhibitor, a PPARα or gamma agonist and a MAP kinase inhibitor.

22. The method of claim 14, wherein the breast cancer brain metastasis is de novo resistant to the estrogen receptor modulator.

23. The method of claim 14, wherein the resistance to the estrogen receptor modulator is acquired.

24. The method of claim 14, wherein the estrogen receptor modulator is a selective estrogen receptor modulator (SERM).

25. The method of claim 24, wherein the SERM is tamoxifen, idoxifene, raloxifene or ICI 182,780.

26. The method of claim 14, wherein the estrogen receptor modulator is an aromatase inhibitor.

27. The method of claim 26, wherein the aromatase inhibitor is anastrozole, letrozole or exemestane.

28. The method of claim 1, wherein the breast cancer brain metastasis is estrogen receptor positive.

* * * * *